United States Patent
Haase et al.

(10) Patent No.: US 8,302,598 B2
(45) Date of Patent: Nov. 6, 2012

(54) BREATHING GAS SUPPLY DEVICE

(75) Inventors: Thorsten Haase, Lübeck (DE); Axel Schmitt, Scharbeutz (DE); Henryk Schnaars, Lübeck (DE); Uwe Schmid, Lübeck (DE); Claus Bunke, Sereetz (DE); Gerald Panitz, Klenzau (DE); Hans-Ulrich Hansmann, Barntiz (DE); Thomas Stepan, Boizenberg (DE)

(73) Assignee: Dräger Medical GmbH, Lübeck (DE)

( * ) Notice: Subject to any disclaimer, the term of this patent is extended or adjusted under 35 U.S.C. 154(b) by 1177 days.

(21) Appl. No.: 12/140,611

(22) Filed: Jun. 17, 2008

(65) Prior Publication Data

US 2009/0020117 A1 Jan. 22, 2009

(30) Foreign Application Priority Data

Jul. 18, 2007 (DE) .......................... 10 2007 033 404

(51) Int. Cl.
A62B 18/00 (2006.01)
(52) U.S. Cl. .......... 128/200.27; 128/204.18; 128/204.21
(58) Field of Classification Search ............. 128/202.27, 128/204.18, 204.21
See application file for complete search history.

(56) References Cited

U.S. PATENT DOCUMENTS

| 5,482,033 | A | * | 1/1996 | Engle et al. | 128/205.19 |
|---|---|---|---|---|---|
| 5,537,997 | A | * | 7/1996 | Mechlenburg et al. | 128/204.23 |
| 6,123,074 | A | * | 9/2000 | Hete et al. | 128/205.11 |
| 6,302,105 | B1 | * | 10/2001 | Wickham et al. | 128/204.18 |
| 6,435,180 | B1 | * | 8/2002 | Hewson et al. | 128/204.18 |
| 6,805,119 | B2 | | 10/2004 | Hoffmann et al. | |
| 7,281,538 | B2 | | 10/2007 | Haase et al. | |
| 7,677,246 | B2 | * | 3/2010 | Kepler et al. | 128/204.18 |
| 8,006,691 | B2 | * | 8/2011 | Kenyon et al. | 128/200.24 |
| 8,015,971 | B2 | * | 9/2011 | Kwok | 128/204.17 |
| 2003/0066526 | A1 | * | 4/2003 | Thudor et al. | 128/203.26 |
| 2004/0055597 | A1 | * | 3/2004 | Virr et al. | 128/203.12 |
| 2005/0123424 | A1 | * | 6/2005 | Wickham et al. | 417/423.14 |
| 2005/0178383 | A1 | * | 8/2005 | Mackie et al. | 128/203.16 |
| 2007/0193580 | A1 | * | 8/2007 | Feldhahn et al. | 128/204.18 |
| 2008/0000474 | A1 | * | 1/2008 | Jochle et al. | 128/204.18 |

FOREIGN PATENT DOCUMENTS

| DE | 101 61 821 C1 | 6/2003 |
|---|---|---|
| DE | 102 19 286 C1 | 7/2003 |

* cited by examiner

*Primary Examiner* — Glenn Richman
(74) *Attorney, Agent, or Firm* — McGlew and Tuttle, P.C.

(57) ABSTRACT

A breathing gas supply device is provided which can be taken apart for cleaning purposes. The breathing gas supply device has a modular design in the form of a breathing gas module (2) and a blower module (3), which are inserted together into a housing module (4).

4 Claims, 3 Drawing Sheets

BREATHING GAS SUPPLY DEVICE

CROSS REFERENCE TO RELATED APPLICATIONS

This application claims the benefit of priority under 35 U.S.C. §119 of German Patent Application DE 10 2007 033 404.6 filed Jul. 18, 2007, the entire contents of which are incorporated herein by reference.

FIELD OF THE INVENTION

The present invention pertains to a breathing gas supply device for an anesthesia apparatus.

BACKGROUND OF THE INVENTION

A respirator for controlling the breathing gas flow in an anesthesia apparatus is known from DE 102 19 286 C1 (corresponding to U.S. Pat. No. 6,805,119 which is hereby incorporated by reference). The respirator comprises, in a layered structure, a breathing gas block, which is traversed by a plurality of gas ducts, a valve plate and a cover, with which the valve plate is braced in relation to the breathing gas block. The breathing gas block is provided with breathing gas ports, via which free breathing gas is supplied to the patient, on the one hand, and, on the other hand, the breathing gas expired by the patient is again taken up. The expired breathing gas is sent via an absorber cartridge, with which the carbon dioxide is removed from the expired gas. The breathing gas thus purified is subsequently supplied again to the patient during the next phase of inspiration. Directional valves in the valve plate ensure a directed breathing gas flow, which leads via an inspiration line to the patient and from the patient back into an expiration line. A breathing gas supply means, which generates the necessary inspiration pressure at the patient, is needed for transporting the breathing gas to the patient. This breathing gas supply means may be integrated in the respirator in the form of a blower, or it is connected to the respirator as a separate reciprocating pump.

A radial blower for supplying breathing gas in a closed breathing circuit is known from DE 101 61 821 C1 (corresponding to U.S. Pat. No. 7,281,538 which is hereby incorporated by reference). The radial blower comprises an upper part carrying breathing gas with a blower rotor (blower wheel or blower impeller), which transports breathing gas from a gas inlet to a gas outlet, and a drive motor, which sets the blower wheel into rotation. A coupling is located between the upper part and the drive motor to make it possible to separate the upper part from the drive motor for disinfection purposes and to connect it to the drive motor again later.

Even though the coupling is dimensioned such that the coupling parts can be reassembled without observing a preferred position, the coupling parts are subject to a certain wear due to the mounting and removal and are additionally stressed by pressure variations during the changeover from the phase of inspiration to the phase of expiration.

SUMMARY OF THE INVENTION

The basic object of the present invention is to improve a breathing gas supply device such that it can be taken apart for cleaning purposes.

According to the invention, a breathing gas supply device is provided with a breathing gas module, which has gas ducts and valves for a directed breathing gas flow in order to supply breathing gas to a patient and to take up the gas expired by the patient. A blower module is provided with a gas inlet, with a gas outlet, with a blower impeller (rotor) and with an electric motor for the blower impeller. The blower module has a housing with the blower module components therein. A plug-type coupling means (plug coupling means) is provided between the breathing gas module and the housing module for detachably connecting the gas inlet and the gas outlet of the blower module to the gas ducts of the breathing gas module. A housing module is provided for accommodating the breathing gas module and the blower module.

The housing module may advantageously have a pot-like depression for accommodating the blower module. The housing module may advantageously have interfaces for the mechanical contact and electrical contact with at least the blower module. The mechanical contact can set the orientation of the blower module relative to the housing and a similar mechanical contact sets the orientation of the breathing gas module relative to the housing module. This sets the orientation of the plug coupling means for a detachable connection of the gas inlet and the gas outlet of the blower module to the gas ducts of the breathing gas module. The housing module may advantageously have a box-like border for receiving the breathing gas module and setting the position with respect to the blower module.

The advantage of the device according to the present invention is that the breathing gas supply device is divided into a breathing gas module and a housing module for accommodating the breathing gas module and the blower module and that the blower module is designed as an encapsulated module such that the blower impeller and the electric drive are arranged together in one housing and the gas inlet and the gas outlet of the blower module are connected to the breathing gas module in the form of a plug coupling. Only a gas connection is established with the plug coupling between the blower module and the breathing gas module, without parts that move in relation to one another being affected hereby. The plug coupling also comprises an electric contacting of the blower module. This can be via a plug/socket connection between the blower module and the housing module. The blower module thus contains all the functional components that are needed for driving the blower rotor, and only the gas ports as well as an electrical interface are needed from the outside. The blower module can thus be cleaned alone via cleaning the gas ports when the device is prepared for operation, without the electric drive having to be removed.

Another advantage is that the drive motor can be connected directly to the blower rotor without an inserted coupling and a more compact design of the blower module can be obtained as a result.

The blower module is connected directly to the breathing gas module via a plug coupling, so that the gas ducts of the breathing gas module are in flow connection with the blower rotor of the blower module. The breathing gas module is then inserted, together with the blower module, into the housing module, which is connected to an anesthesia apparatus.

To accommodate the blower module, the housing module has a pot-like depression, into which the blower module is inserted. Electric contacts, with which the electrical connection is established between the housing module and the blower module, are arranged at the bottom of the depression. The housing module has, moreover, a box-like border, which surrounds the breathing gas module in the mounted state.

An exemplary embodiment is shown in the drawings and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
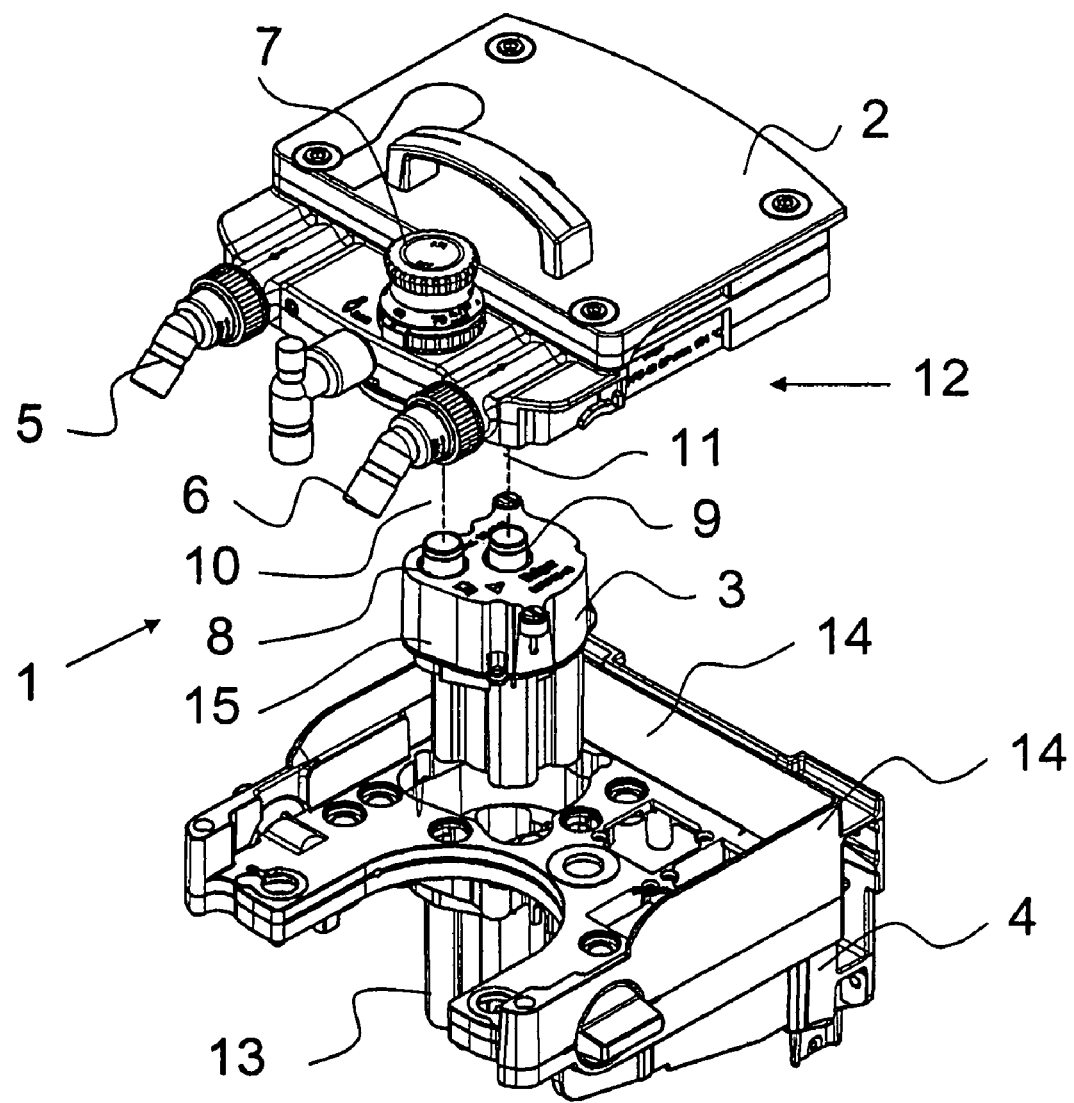
FIG. 1 is a perspective view of a breathing gas supply device.

Referring to the drawings in particular, FIG. 1 is a perspective view of a breathing gas supply device 1, comprising a breathing gas module 2 (a structural unit), a blower module 3 (a structural unit) and a housing module 4 (a structural unit), which is designed to accommodate the blower module 3 and the breathing gas module 2.

The breathing gas module 2 has breathing gas ports 5, 6, with which the connection to a patient, not shown, can be established via flexible breathing tubes, which are likewise not shown. The breathing gas ports 5, 6 are connected to one another in the known manner via internally extending gas ducts and directional valves, which are not shown in more detail. The breathing gas module 2 has an adjustable pressure relief valve 7, with which the breathing pressure building up in the system can be limited to a predetermined value.

The blower module 3 has, on its upper side, a gas inlet 9 and a gas outlet 8, which are introduced into corresponding mounting holes 10, 11 on the underside of the breathing gas module 2. Together with the mounting holes (sockets) 10, 11, the gas inlet 9 and the gas outlet 8 form a plug coupling (plug and socket coupling means or plug coupling means) 12, with which a flow connection is established between the gas ducts of the breathing gas module 2 and of the blower module 3.

The housing module 4 has a pot-like depression 13, which is used to receive the blower module 3, and a box-like border 14, into which the breathing gas module 2 is inserted.

Figure 2:
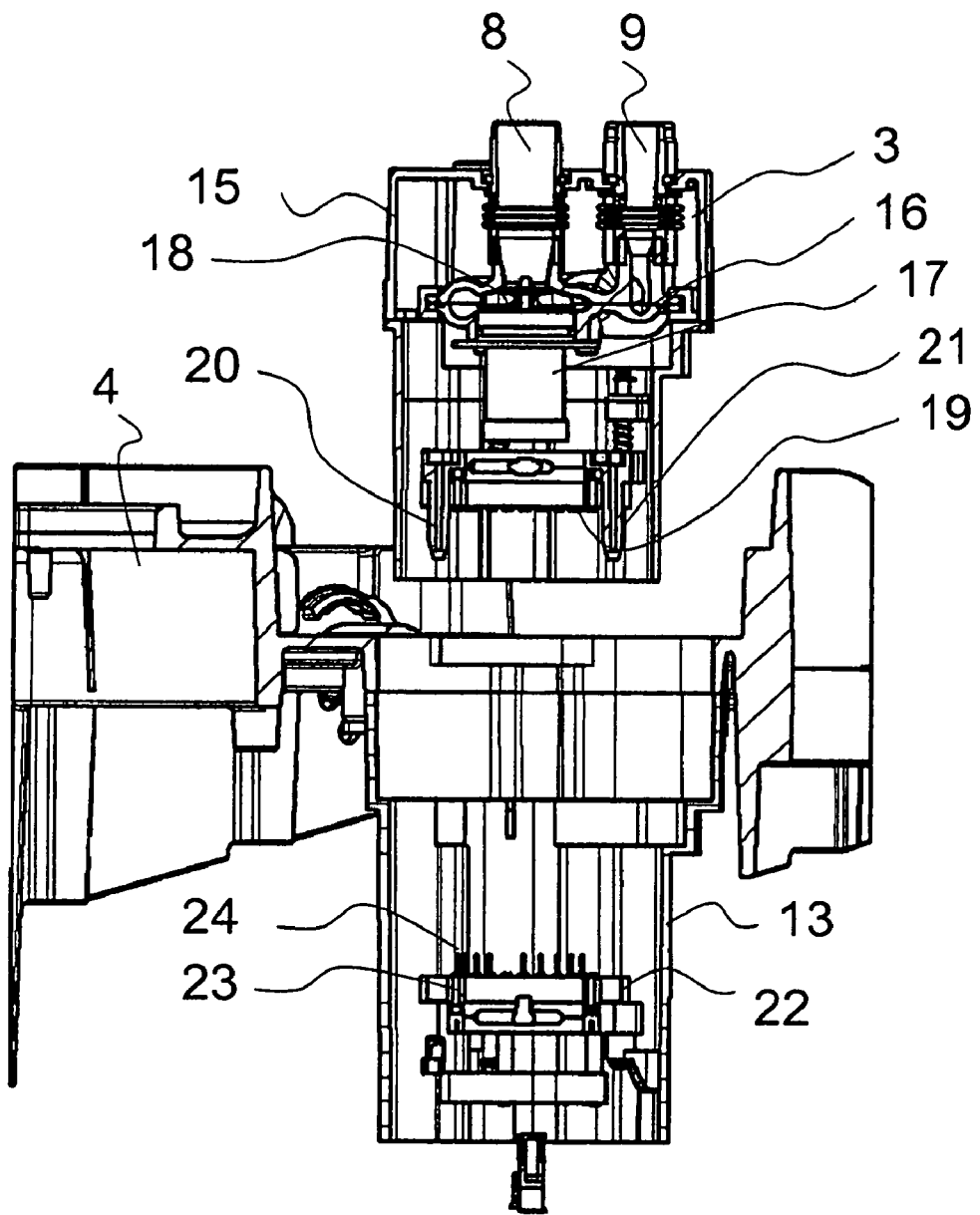
FIG. 2 is a sectional view of the blower module and of the housing module at the connection site between the blower module and the housing module.
Figure 3:
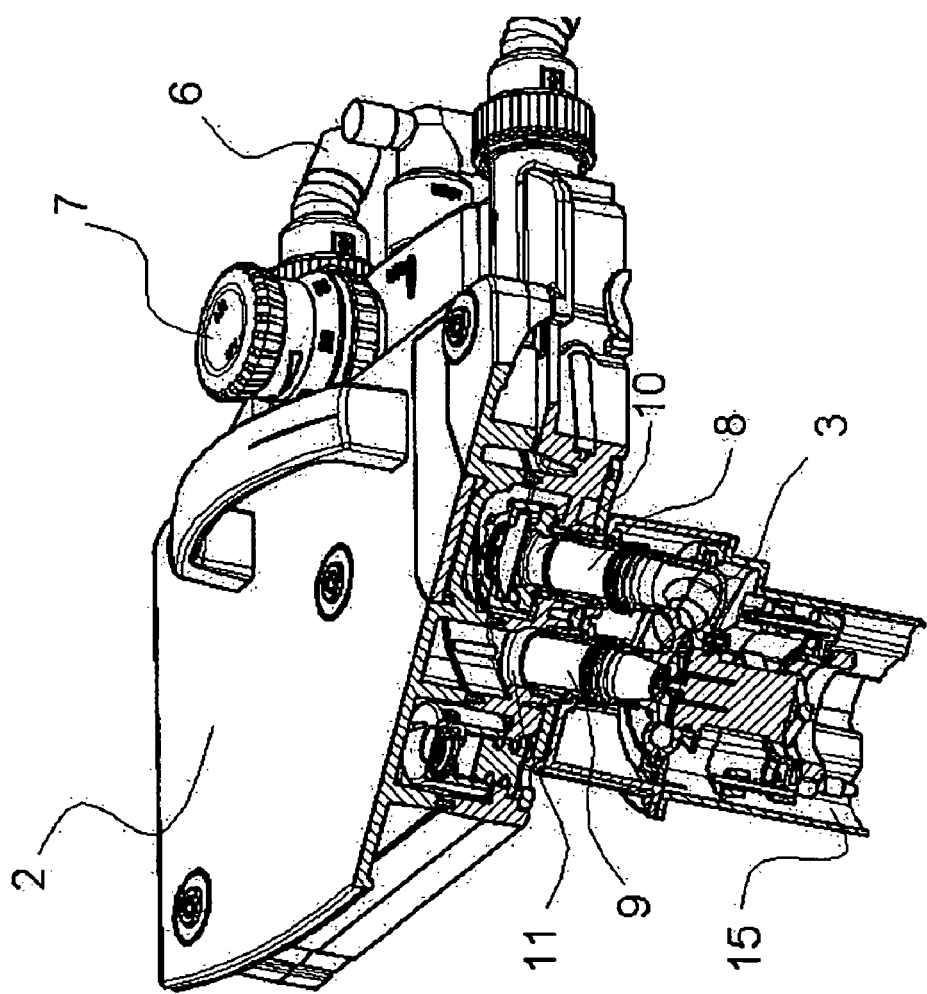
FIG. 3 is a partially sectional view showing details of the blower module having a gas inlet and a gas outlet.

FIG. 2 shows a sectional view of the blower module 3 and of the housing module 4 in the area of the pot-like depression 13. Identical components are designated by the same reference numbers as in FIG. 1. The gas inlet 9 and the gas outlet 8, which are connected internally to one another via a flow channel 16, are arranged on the upper side in a housing 15 of the blower module 3. A blower impeller 18, which is driven by an electric motor 17 and which supplies the breathing gas from the gas inlet 9 to the gas outlet 8, is arranged in the flow channel 16. Contact jacks 19, with which an electrical connection is established with the blower module 3, are located on the underside of the housing 15. Centering pins 20, 21 are provided which mesh with corresponding centering holes 22, 23 on the pot-like depression 13. The centering pins 20, 21 are provided on the outside of the contact jacks 19 to center the blower module 3 in relation to the housing module 4. Contact pins 24, which have a design corresponding to that of the contact jacks 19 and which establish the electrical connection between the housing module 4 and the blower module 3 when the blower module 3 has been fully inserted into the pot-like depression 13, are also located at this site.

While a specific embodiment of the invention has been shown and described in detail to illustrate the application of the principles of the invention, it will be understood that the invention may be embodied otherwise without departing from such principles.

LIST OF REFERENCE NUMBERS

1 Breathing gas supply device
2 Breathing gas module
3 Blower module
4 Housing module
5,6 Breathing gas ports
7 Pressure relief valve
8 Gas outlet
9 Gas inlet
10,11 Mounting hole
12 Plug coupling
13 Pot-like depression
14 Box-like border
15 Housing
16 Flow duct
17 Electric motor
18 Blower impeller
19 Contact jacks
20,21 Centering pins
22,23 Centering holes
24 Contact pins

What is claimed is:

1. A breathing gas supply device comprising:
a breathing gas module comprising gas ducts and valves connected to an inspiration breathing gas port and to an expiration breathing gas port for a directed breathing gas flow in order to supply breathing gas to a patient and to take up gas expired by the patient;
a blower module comprising a housing, a gas inlet, a gas outlet, a blower impeller and an electric motor for driving said blower impeller in rotation, said housing defining a closed interior with said blower impeller and an electric motor in said closed interior;
a housing module having surface features for receiving said blower module and setting an orientation of said blower module relative to said housing module and having surface features for receiving said breathing gas module and setting an orientation of said breathing gas module relative to said housing module and relative to said blower module; and
a plug and socket coupling arrangement with plugs or sockets of said gas inlet and gas outlet of said blower module and with plugs or sockets connected to said gas ducts and valves of said breathing gas module for detachably connecting said gas inlet and said gas outlet of said blower module to said gas ducts of said breathing gas module via said plug and socket coupling arrangement.

2. A breathing gas supply device in accordance with claim 1, wherein said housing module has electrical contact interfaces with said blower module and wherein said surface features of said housing module include mechanical interfaces with said blower module.

3. A breathing gas supply device in accordance with claim 2, wherein said surface features of said housing module comprise a box-like border for receiving said breathing gas module.

4. A breathing gas supply device in accordance with claim 1, wherein said surface features of said housing module include a pot-shaped depression for accommodating said blower module.

* * * * *